United States Patent [19]

Yoshida et al.

[11] 4,023,956
[45] May 17, 1977

[54] AMIDE PHOSPHOROTHIOLATE HERBICIDES

[75] Inventors: Ryo Yoshida, Minoo; Takeo Satomi; Kunio Mukai, both of Nishinomiya; Masachika Hirano, Ibaraki, all of Japan

[73] Assignee: Sumitomo Chemical Company, Limited, Osaka, Japan

[22] Filed: Sept. 9, 1975

[21] Appl. No.: 611,606

[30] Foreign Application Priority Data

Sept. 24, 1974 Japan .............................. 49-110264

[52] U.S. Cl. .................................. 71/87; 260/943; 260/979; 424/211
[51] Int. Cl.² ...................... A01N 9/36; C07F 9/165
[58] Field of Search ....................... 260/943; 71/87

[56] References Cited

UNITED STATES PATENTS

| | | |
|---|---|---|
| 3,102,019 | 8/1963 | Speziale et al. ............... 71/87 X |
| 3,385,689 | 5/1968 | Richter .............................. 71/87 |
| 3,806,560 | 4/1974 | Kishino et al. .................. 260/943 |
| 3,845,171 | 10/1974 | Beriger ............................ 260/943 |

*Primary Examiner*—Richard L. Raymond
*Attorney, Agent, or Firm*—Wenderoth, Lind & Ponack

[57] ABSTRACT

Compounds of the formula

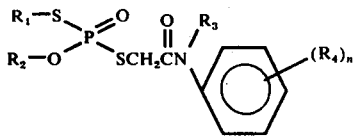

where $R_1$ is lower alkenyl, optionally substituted by chlorine or bromine, or $R_1$ is alkoxyalkyl; $R_2$ and $R_3$ are lower alkyl; $R_4$ is lower alkyl, lower alkoxy or halogen; and $n$ is zero or an integer of 1–5, which are useful as herbicides, insecticides, acaricides and nematocides.

8 Claims, No Drawings

AMIDE PHOSPHOROTHIOLATE HERBICIDES

The present invention relates to new compounds, herbicides, insecticides, acaricides and nematocides characterized by containing a new phosphorothiolate derivative as an active ingredient and the preparation thereof.

More particularly, the present invention provides (1) a new phosphorothiolate derivative of the formula;

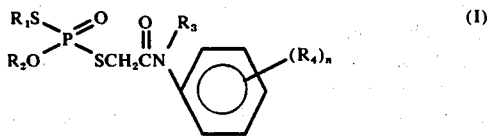

wherein $R_1$ is a lower alkenyl, a chlorine- or bromine-substituted lower alkenyl or an alkoxyalkyl group; $R_2$ is a lower alkyl group; $R_3$ is a lower alkyl group; $R_4$ is a lower alkyl, a lower alkoxy group or a halogen atom; $n$ is zero or an integer of 1 to 5, (2) the preparation of the compound of the formula (I) characterized by condensing a salt of thiophosphate of the formula;

wherein $R_1$ and $R_2$ are the same as defined above, and M is an alkali metal with a halogenated acetoamide compound of the formula;

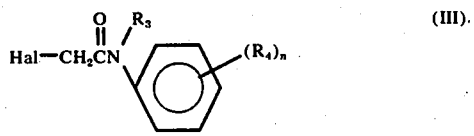

wherein $R_3$, $R_4$ and $n$ are the same as defined above, and Hal is a halogen atom, and (3) herbicidal, insecticidal, acaricidal and nematocidal compositions containing the compound of the formula (I) as an active ingredient.

A preferred group of the compounds of the formula (I) is as follows:

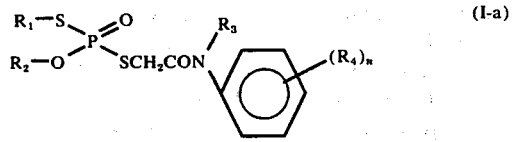

wherein $R_1$ is a $C_3$–$C_4$ alkenyl, a chlorine- or bromine-substituted $C_3$ alkenyl, or a $C_1$–$C_2$ alkoxy $C_1$–$C_3$ alkyl group; $R_2$ is a $C_1$–$C_4$ alkyl group; $R_3$ is a $C_1$–$C_4$ alkyl group; $R_4$ is a $C_1$–$C_2$ alkyl, a methoxy group or a chlorine atom; $n$ is zero or an integer of 1 to 5.

And a preferred compound as a herbicide is as follows:

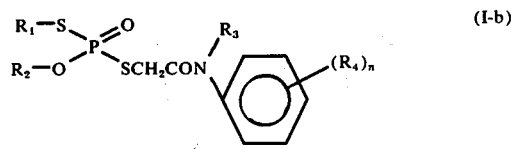

wherein $R_1$ is a $C_3$–$C_4$ alkenyl, a chloroallyl, a bromoallyl or a $C_1$–$C_2$ alkoxy $C_1$–$C_2$ alkyl group; $R_2$ is a $C_1$–$C_3$ alkyl group; $R_3$ is a methyl group; $n$ is zero.

The new active ingredient of the present invention displays a strong herbicidal activity not only when used in both a pre-emergence treatment and a foliage treatment of weeds, but also on various kinds of weed including grassy weeds such as barnyard glass (*Echinochloa crusgalli*), large crabgrass (*Digitaria sanguinalis*), goose grass (*Eleusine indica*), water foxtail (*Alopecurus aequalis*) and annual bluegrass (*Poa annua*); broad-leaved weeds such as redroot pigweed (*Amaranthus retroflexus*), common purslane (*Portulaca oleracea*), smart weed sp. (*Poligonum* sp.), common lambsquarter (*Chenopodium album*), and weeds in paddy field such as false pimpernel (*Linderna pyxidaria*), monochoria (*Monochroia viaginalis presl.*) and toothcut (*Rotala indica Koehue*); sedge weeds such as nutsedge sp. (*Cyperus difforuds*) and slender spikerush (*Eleocharis acicularis*).

One of the most important properties of herbicides is that they be able to display a herbicidal activity on various kinds of weed, because, if they can control most kinds of weed but not a few other kinds of weeds, the remaining weeds will often grow and do harm to crops.

Therefore, the compounds of the present invention, which can display a strong herbicidal activity on more kinds of weed, can be said to be most suitable for a herbicide.

As for the insecticidal effect of the present compounds, they have a strong controlling effect on insects injurious to agriculture such as aphids stemborers and armyworms and cutworms; insects injurious to sanitation such as cockroaches, and houseflies; insects injurious to stored cereals; mites; and nematodes. Consequently they are effectively used as a herbicide, insecticide, acaricide and nematocide.

The present invention (1) relates to a herbicide, insecticide, acaricide and nematocide, based on the above-mentioned information, which are the compounds represented by the formula (I) and may be contained as an active ingredient in compositions intended for these uses.

As a prior art relating to the present invention there may be mentioned U.S. Pat. No. 3,385,689 wherein are disclosed, for example, compounds of the formula:

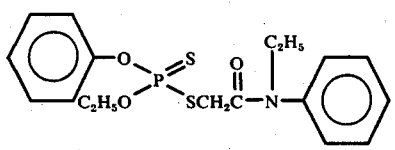

which have herbicidal properties.

We have investigated the herbicidal activity of various derivatives of these phosphorothiolate compounds and have found that the compound of the following structure:

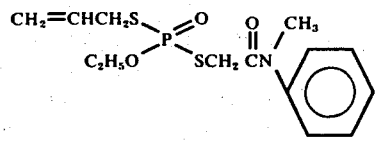

has excellent herbicidal efficacy. It has been surprising to find that the compounds of the formula (I) are excellent herbicides. Especially when a pre-emergence or pre-plant application is made, they show remarkably excellent effect in killing weeds and yet they do not appear to have any phytotoxicity to cultivated plants.

The present invention (3) relates to a herbicidal, insecticidal, acaricidal and nematocidal composition, based on the above-mentioned information, which contains the compound represented by the formula (I) as an active ingredient.

The present invention (2) relates to a method for producing a compound of the formula (I) with herbicidal, insecticidal, acaricidal and nematocidal activity characterized in that phosphorodithiolate of the formula (I);

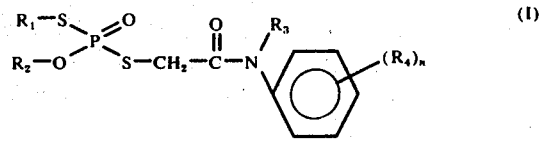

wherein $R_1$, $R_2$, $R_3$, $R_4$ and $n$ are the same as defined above, is obtained by condensing a salt of dithiophosphate of the formula (II);

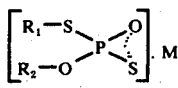

wherein $R_1$, $R_2$ and M are the same as defined above, with a halogenated acetoamide compound of the formula (III);

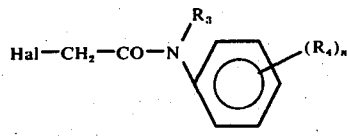

wherein Hal, $R_3$, $R_4$ and $n$ are the same as defined above.

The present invention (2) can preferably be carried out by condensing a salt of dithiophosphate of the formula (II) with halogenated acetamide compound of the formula (III) in the presence of solvents such as water, alcohols, ketones and if possible solvents which can dissolve both starting materials completely therein. The reaction temperatures and reaction times vary depending upon the kinds of solvent and starting material, and in general the reaction can satisfactorily proceed at 20 to 100° C. for one to several hours. On completion of the reaction, the objective products can readily be obtained in a very high purity by conventional treatments; however, if necessary, they can further be purified by columnchromatography.

Some examples of the starting materials, i.e. dithiophosphate salts and halogenated acetamides, which are used in the practice of the present invention will be shown as follows.

First, examples of dithiophosphate salt are as follows, which are only illustrative but not limitative thereto:

potassium O-ethyl-S-allylphosphorodithioate
potassium O-ethyl-S-methallylphosphorodithioate
potassium O-ethyl-S-2-ethoxyethylphosphorodithioate
potassium O-ethyl-S-2-methoxyethylphosphorodithioate
potassium O-ethyl-S-2-chloro-2-propenylphosphorodithioate
potassium O-ethyl-S-2-bromo-2-propenylphosphorodithioate
potassium O-ethyl-S-3-chloro-2-propenylphosphorodithioate
potassium O-ethyl-S-2-butenylphosphorodithioate
potassium O-ethyl-S-3-methoxypropylphosphorodithioate
potassium O-ethyl-S-3-ethoxypropylphosphorodithioate
sodium O-ethyl-S-allylphosphorodithioate
sodium O-ethyl-S-methallylphosphorodithioate
sodium O-ethyl-S-2-ethoxyethylphosphorodithioate
sodium O-ethyl-S-2-methoxyethylphosphorodithioate
sodium O-ethyl-S-2-chloro-2-propenylphosphorodithioate
sodium O-ethyl-S-2-bromo-2-propenylphosphorodithioate
sodium O-ethyl-S-3-chloro-2-propenylphosphorodithioate
potassium O-n-propyl-S-methallyphosphorodithioate
potassium O-n-propyl-S-2-ethoxyethylphosphorodithioate
potassium O-n-propyl-S-allylphosphorodithiate
potassium O-n-butyl-S-allylphosphorodithioate
potassium O-n-butyl-S-methallylphosphorodithioate Examples of halogenated acetamide compound are as follows, which are only illustrative but not limitative thereto:

N-methyl-aniline-α-chloroacetamide
N-ethyl-aniline-α-chloroacetamide
N-(n)-propyl-aniline-α-chloroacetamide
N-(n)-butyl-aniline-α-chloroacetamide
N-methyl-m-toluidine-α-chloroacetamide
N-methyl-o-toluidine-α-chloroacetamide
N-methyl-p-toluidine-α-chloroacetamide
N-ethyl-m-toluidine-α-chloroacetamide
N-ethyl-o-toluidine-α-chloroacetamide
N-ethyl-p-toluidine-α-chloroacetamide
N-methyl-p-anisidine-α-chloroacetamide
N-methyl-o-anisidine-α-chloroacetamide
N-methyl-p-chloroaniline-α-chloroacetamide
N-methyl-aniline-α-bromoacetamide Next, some representative examples of the organic phosphoric acid ester of the present invention will concretely be shown as follows:

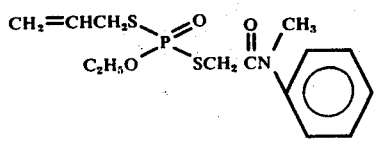

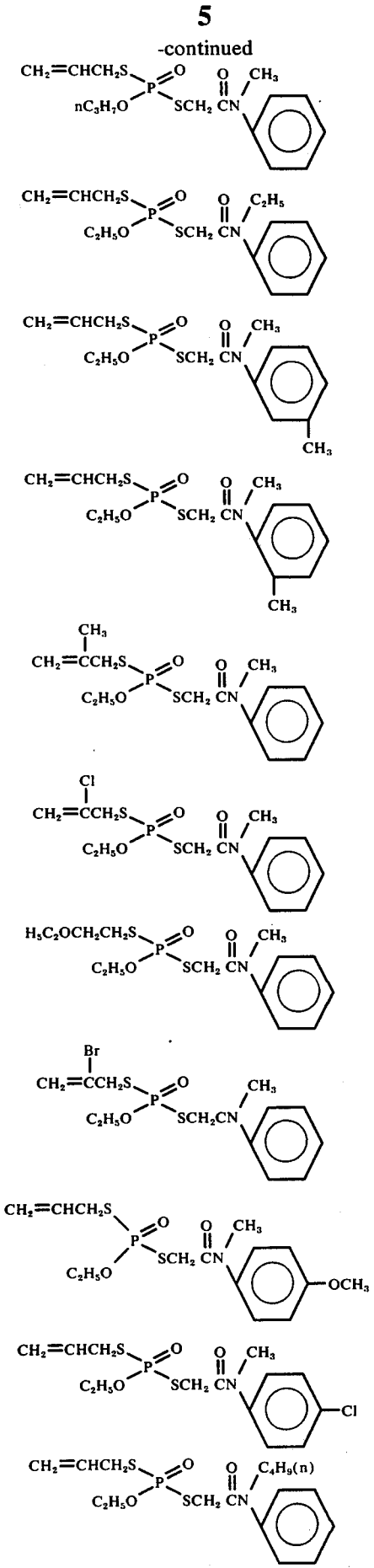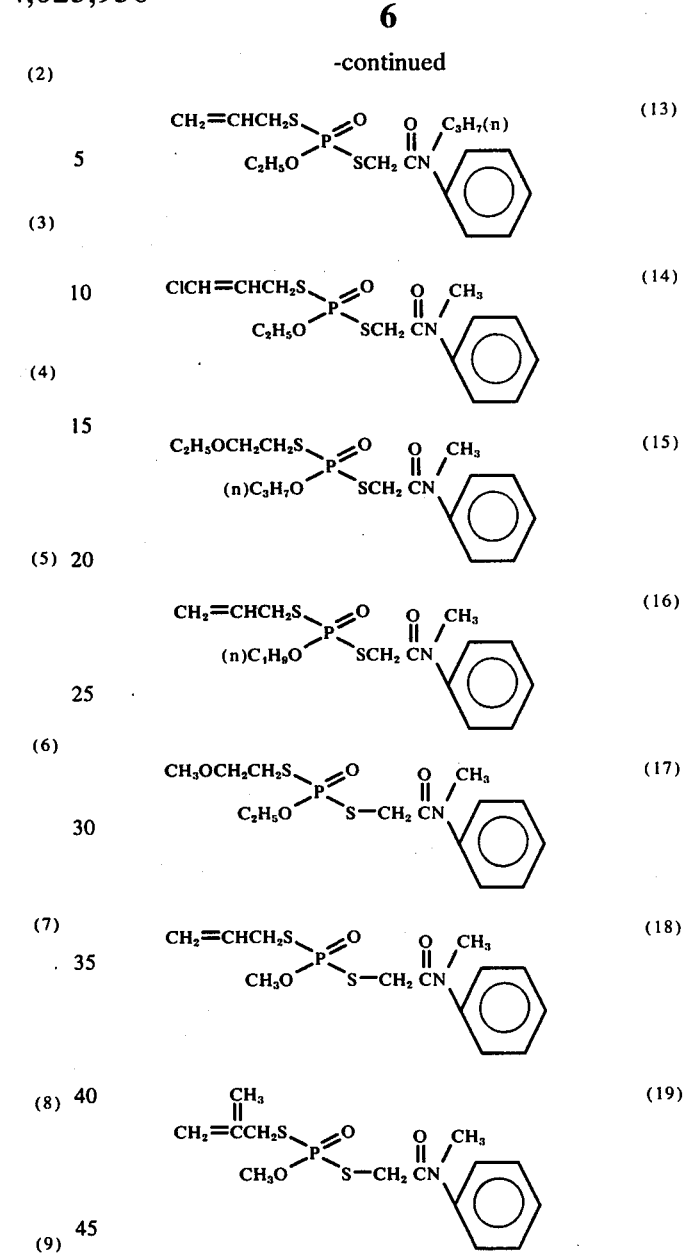

The compounds of the present invention, as described above, display a strong herbicidal activity on various kinds of weed; however one of the most noticeable features thereof is their herbicidal activity on more kinds of weed in addition to their strong herbicidal activity.

Moreover, the compounds of the present invention have other excellent properties as a herbicide, for example, a long persistency, an activity in both a preemergence treatment and a foliage treatment of weeds, and a selectivity which renders them suitable for use in many crops such as rice plant, radish, soy bean, sugar beet, cotton, pea, tomato, lettuce, wheat and corn. The present compounds are also useful as a herbicide for use in paddy rice fields, crops of cereals and vegetables, orchards, turfs, pasture lands, woods and forests and non-crop lands.

The features of the present compounds as an insecticide, acaricide and nematocide are that they have a controlling effect on various kinds of insects, a wide insecticidal spectrum, a particularly strong lethal effect on insects of Lepidoptera such as stem-borers and armyworms and cutworms, a strong lethal effect in both a spraying or dusting and a soil treatment, and a long persistency.

The present compounds, in actual application thereof, may be used as they are or may be used in any preparation form of dusts, granules, fine granules, wettable powders and emulsifiable concentrates. In formulating those preparations, there are used solid carriers including talc, bentonite, clay, kaolin, diatomaceous earth, vermiculite and calcium hydroxide; and liquid carriers including benzene, alcohols, acetone, xylene, methylnaphthalene, dioxane and cyclohexanone.

In actual application, the activity of the present compounds may be enhanced and their effectiveness ensured by using them in combination with surfactants such as spreaders for agriculture. It is also possible to use the present compounds in combination with agricultural chemicals such as fungicides, microbial insecticides, prechroide type insecticides, other insecticides and other herbicides, or with fertilizers.

The compositions of the present invention will be illustrated with reference to the following preparation examples.

PREPARATION 1

25 parts of the compound (1) above, 5 parts of a surfactant of polyoxyethylene acetylallylester type and 70 parts of talc were thoroughly mixed together by pulverizing to obtain a wettable powder.

PREPARATION 2

30 parts of the compound (3), 20 parts of a surfactant of polyethylene glycolester type and 50 parts of cyclohexanone were thoroughly mixed together to obtain an emulsifiable concentrate.

PREPARATION 3

5 parts of the compound (7), 40 parts of bentonite, 50 parts of clay and 5 parts of sodium lignosulfonate were thoroughly mixed together by pulverizing, sufficiently kneaded with water, granulated and dried to obtain granules.

PREPARATION 4

3 parts of the compound (8) and 97 parts of clay were thoroughly mixed together by pulverizing to obtain a dust.

PREPARATION 5

5 parts of the compound (4), 4 parts of sodium lignosulfonate, 86 parts of clay and 5 parts of water were thoroughly kneaded in a ribbon mixer and dried to obtain fine granules.

PREPARATION 6

25 parts of the compound (6), 5 parts of a surfactant of polyoxyethylene acetylallylester type and 70 parts of talc were thoroughly mixed together by pulverizing to obtain a wettable powder.

The present invention will be illustrated in more detail with reference to the following test examples, in which the names of the compounds are represented by the numbers of the compounds exemplified above.

Test Example 1: Pre-emergence application.

Seeds of barnyard grass (*Echinochloa crus-galli*) and large crabgrass (*Digitaria sanguinalis*) as representatives of grassy weeds and those of radish, redroot pigweed (*Amaranthus retroflexus*), common purslane (*Portulaca oleracea*) and common lambsquarter (*Chenopodium album*) as representatives of broad-leaved weeds were individually sowed in flower pots of about 10 cm. in diameter. After covering the seeds with soil, test compounds as shown in Table 1 were individually applied to the soil. Thereafter the plants were grown in a green house and 20 days after application the herbicidal effects of the compounds were observed, the results of which are as shown in Table 1.

Herbicidal effects were evaluated by the numerals ranging from 0 (not damaged) to 5 (completely killed). All the test compounds were used in the form of wettable powder and diluted with water before application.

Table 1

| Comp. No. | Amount applied (g/a) | Barn-yard grass | Large crab-grass | Radish | Red-root pig-weed | Common purs-lane | Common lambs-quarter |
|---|---|---|---|---|---|---|---|
| 1 | 40 | 5 | 5 | 0 | 5 | 5 | 5 |
|  | 20 | 5 | 5 | 0 | 5 | 5 | 5 |
|  | 10 | 5 | 5 | 0 | 5 | 5 | 5 |
| 2 | 40 | 5 | 5 | 0 | 5 | 5 | 5 |
|  | 20 | 5 | 5 | 0 | 5 | 5 | 5 |
|  | 10 | 5 | 5 | 0 | 4 | 4 | 4 |
| 3 | 40 | 5 | 5 | 0 | 5 | 5 | 5 |
|  | 20 | 5 | 5 | 0 | 5 | 4 | 5 |
|  | 10 | 4 | 4 | 0 | 4 | 3 | 3 |
| 4 | 40 | 5 | 5 | 0 | 5 | 5 | 5 |
|  | 20 | 5 | 5 | 0 | 5 | 5 | 5 |
|  | 10 | 5 | 5 | 0 | 4 | 4 | 4 |
| 5 | 40 | 5 | 5 | 0 | 5 | 5 | 5 |
|  | 20 | 5 | 5 | 0 | 4 | 4 | 4 |
|  | 10 | 3 | 4 | 0 | 3 | 2 | 2 |
| 6 | 40 | 5 | 5 | 0 | 5 | 5 | 5 |
|  | 20 | 5 | 5 | 0 | 4 | 4 | 4 |
|  | 10 | 5 | 5 | 0 | 3 | 3 | 4 |
| 7 | 40 | 5 | 5 | 0 | 5 | 5 | 5 |
|  | 20 | 5 | 5 | 0 | 4 | 4 | 4 |
|  | 10 | 5 | 5 | 0 | 3 | 3 | 3 |
| 8 | 40 | 5 | 5 | 0 | 5 | 5 | 5 |
|  | 20 | 5 | 5 | 0 | 4 | 4 | 4 |
|  | 10 | 5 | 5 | 0 | 4 | 4 | 4 |
| 9 | 40 | 5 | 5 | 0 | 5 | 5 | 5 |
|  | 20 | 5 | 5 | 0 | 4 | 4 | 3 |
|  | 10 | 5 | 5 | 0 | 4 | 2 | 3 |
| pcp[1] | 100 | 3 | 4 | 4 | 4 | 4 | 4 |
|  | 50 | 2 | 2 | 1 | 2 | 2 | 2 |
| Zytron[2] | 40 | 4 | 3 | 0 | 1 | 2 | 2 |
|  | 20 | 3 | 1 | 0 | 0 | 1 | 0 |
| Compound[3] | 40 | 5 | 5 | 0 | 2 | 2 | 1 |
|  | 20 | 4 | 4 | 0 | 1 | 0 | 0 |
|  | 10 | 2 | 3 | 0 | 0 | 0 | 0 |

Note [1] Chemical structure

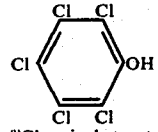

[2] Chemical structure

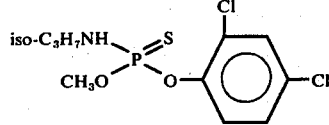

[3] Chemical structure

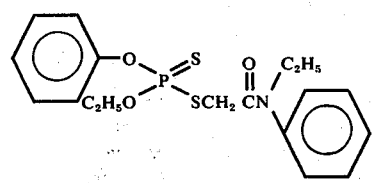

Test Example 2: Water application

Wagner pots of 14 cm. in diameter, which had been packed with 1.5 kg. of paddy field soil, were brought into the environment of paddy fields. To the pots were transplanted rice seedings at the 3-leave stage. Further, seeds of barnyard grass (*Echinochloa crus-galli*) were sowed in the pots and required amounts of test compounds were applied to the soil under water lodged condition. 25 days after application, the degrees of herbicidal activity and phytotoxity were investigated on above-mentioned plants which had been transplanted and sowed, and on broad-leaved weeds, e.g., monochoria (*Monochoria viaginalis Presl.*), false pimpernel (*Linderna pyxidaria*) and toothcup (*Rotala indica Koehue*), which had been spontaneously germinated. The test compounds were used in the form of wettable powder. The results obtained are as shown in Table 2. The herbicidal effects and the phytotoxity were evaluated as follows by the numerals ranging from 0 to 5.

Table 2

| | Effect on plants |
|---|---|
| 0 | no effect |
| 1 | very slightly affected |
| 2 | slightly affected |
| 3 | moderately affected |
| 4 | considerably affected |
| 5 | completely killed |

| Compound No. | Amount applied (g/a) | Herbicidal effects | | Phytotoxicity on rice |
|---|---|---|---|---|
| | | Barnyard grass | Broad-leaved weeds | |
| 1 | 40 | 5 | 5 | 0 |
| | 20 | 5 | 5 | 0 |
| | 10 | 5 | 5 | 0 |
| 2 | 40 | 5 | 5 | 0 |
| | 20 | 5 | 5 | 0 |
| | 10 | 5 | 5 | 0 |
| 3 | 40 | 5 | 5 | 0 |
| | 20 | 5 | 5 | 0 |
| | 10 | 5 | 5 | 0 |
| 4 | 40 | 5 | 5 | 0 |
| | 20 | 5 | 5 | 0 |
| | 10 | 5 | 5 | 0 |
| 5 | 40 | 5 | 5 | 0 |
| | 20 | 5 | 5 | 0 |
| | 10 | 5 | 5 | 0 |
| 6 | 40 | 5 | 5 | 0 |
| | 20 | 5 | 5 | 0 |
| | 10 | 5 | 5 | 0 |
| 7 | 40 | 5 | 5 | 0 |
| | 20 | 5 | 5 | 0 |
| | 10 | 5 | 5 | 0 |
| 8 | 40 | 5 | 5 | 0 |
| | 20 | 5 | 5 | 0 |
| | 10 | 5 | 5 | 0 |
| 9 | 40 | 5 | 5 | 0 |
| | 20 | 5 | 5 | 0 |
| | 10 | 5 | 5 | 0 |
| 10 | 40 | 5 | 5 | 0 |
| | 20 | 5 | 5 | 0 |
| | 10 | 5 | 5 | 0 |
| 11 | 40 | 5 | 5 | 0 |
| | 20 | 5 | 5 | 0 |
| | 10 | 5 | 5 | 0 |
| 12 | 40 | 5 | 5 | 0 |
| | 20 | 5 | 5 | 0 |
| | 10 | 5 | 5 | 0 |
| 14 | 40 | 5 | 5 | 0 |
| | 20 | 5 | 5 | 0 |
| | 10 | 5 | 5 | 0 |
| 15 | 40 | 5 | 5 | 0 |
| | 20 | 5 | 5 | 0 |
| | 10 | 5 | 5 | 0 |
| 16 | 40 | 5 | 5 | 0 |
| | 20 | 5 | 5 | 0 |
| | 10 | 5 | 5 | 0 |
| pcp (control) | 100 | 5 | 5 | 3 |
| | 50 | 4 | 5 | 2 |
| Zytron (control) | 40 | 3 | 3 | 0 |
| | 20 | 1 | 2 | 0 |
| Nip[1] (control) | 40 | 5 | 5 | 4 |
| | 20 | 5 | 5 | 2 |
| | 40 | 5 | 3 | 0 |
| Compound A (control) | 20 | 4 | 2 | 0 |
| | 10 | 2 | 1 | 0 |

Note: [1]Chemical structure

Table 2-continued

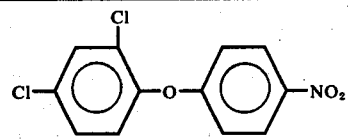

Test Example 3: Lethal effect on carmine mite (Tetranychus telarius)

About 50 carmine mite adults were made parasitic on leaves of potted kidney beans at a 2-leave stage which had elapsed 10 days after sowing. After a week, the present compounds in the form of a 25 % wettable powder were each applied in a 200 fold dilute solution. After standing for another week the degree of damage was observed, the results of which are as shown in Table 3.

Table 3

| Compound No. | Degree of damage |
|---|---|
| 1 | + |
| 2 | + |
| 3 | −∼+ |
| 4 | + |
| 5 | −∼+ |
| 6 | − |
| 7 | − |
| 8 | − |
| No treatment | ++++ |
| Smite* (control) | + |

*Chemical structure

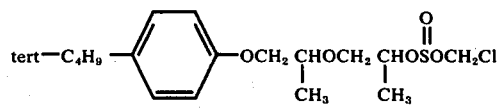

Note:
−: damage is hardly increased.
+: damage is slightly increased.
++: damage is fairly increased.
+++: damage is heavily increased.
++++: completely damaged.

Test Example 4: Effect on nematode 0.5 ml. of a nematode-containing aqueous solution separated from food according to Baermann's method was placed in a test tube with ground stopper containing 0.5 ml. of an aqueous dilute solution of each emulsifiable concentrate of the present compounds. The concentration of the active ingredient in the mixture was adjusted to 500 p.p.m. After 24 hours, the number of dead and live nematodes were observed microscopically to calculate the mortality rate. The results are as shown in Table 4.

Table 4

| Compound No. | Mortality (%) |
|---|---|
| 1 | 70.8 |
| 2 | 86.3 |
| 3 | 100 |
| 4 | 72.5 |
| 5 | 81.0 |
| 6 | 100 |
| 7 | 100 |
| 8 | 100 |

Test Example 5

Adzuki bean weevils (*Callosobruchus chinensis*) within one day after emergence were dipped for 1 minute in each emulsion prepared by diluting 250 times with water the test compounds in the form of emulsifiable concentrates. After 24 hours, the number of live and dead weevils were observed.

The mortality rates produced by all compounds were more than 80 %.

The synthetic method according to the present invention will be illustrated with reference to the following examples which are only illustrative but not limitative thereto.

EXAMPLE 1: (Compound No. 1)

To a solution of 23.6 g. of potassium 0-ethyl-S-allyl-phosphorodithioate in 100 ml. of ethylalcohol, were added 18.3 g. of N-methylaniline-α-chloroacetamide, and then the mixture was refluxed under stirring for 2 hours. After removal of ethylalcohol under reduced pressure, the residue was dissolved in benzene. The resulting solution was washed with a 5 % sodium carbonate solution and then water. Thereafter benzene was distilled off to obtain 31.4 g. of yellow and oily 0-ethyl-S-allyl-S-(N-methyl-N-phenylcarbamoylmethyl)-phosphorodithiolate ($n_D^{20.5}$ 1.5638).

| Elemental analysis Calculated (%) (as $C_{14}H_{20}NO_3PS_2$) | Found (%) |
|---|---|
| P | 8.97 | 8.53 |
| C | 48.67 | 49.07 |
| H | 5.84 | 6.16 |
| N | 4.06 | 4.12 |

Example 2: (Compound No. 2)

To a solution of 30.0 g. of potassium O-n-propyl-S-allylphosphorodithioate in 100 ml. of acetone, were added 18.3 g. of N-methylaniline-α-chloroacetoamide, and then the mixture was refluxed under stirring for 2 hours, and thereafter treated in the same manner as described in Example 1. 31.5 g. of yellow and oily 0-(n)propyl-S-allyl-S-(N-methyl-N-phenylcarbamoylmethyl)-phosphorodithiolate ($n_D^{18.0}$ 1.5641) were obtained.

| Elemental analysis: Calculated (%) (as $C_{15}H_{22}NO_3PS_2$) | Found (%) |
|---|---|
| P | 8.62 | 8.65 |
| C | 50.12 | 50.17 |
| H | 6.18 | 6.21 |
| N | 3.90 | 3.94 |

| Example No. | Compound No. | Yield | Refractive index | | Elemental analysis Calculated (%) | Found (%) |
|---|---|---|---|---|---|---|
| 3 | 3 | 81.0 | $n_d^{20.5}$ 1.5570 | C | 50.11 | 50.15 |
| | | | | H | 6.18 | 6.49 |
| | | | | N | 3.90 | 3.89 |
| | | | | P | 8.62 | 8.34 |
| 4 | 4 | 83.5 | $n_d^{20.5}$ 1.5609 | C | 50.11 | 49.96 |
| | | | | H | 6.18 | 6.46 |
| | | | | N | 3.90 | 4.01 |
| | | | | P | 8.62 | 8.38 |
| 5 | 5 | 82.6 | $n_D^{21.0}$ 1.5649 | C | 50.11 | 49.88 |
| | | | | H | 6.18 | 6.44 |
| | | | | N | 3.90 | 3.81 |
| | | | | P | 8.62 | 8.31 |
| 6 | 6 | 83.4 | $n_D^{18.0}$ 1.5663 | C | 50.12 | 50.18 |
| | | | | H | 6.18 | 6.17 |
| | | | | N | 3.90 | 4.00 |
| | | | | P | 8.62 | 8.70 |
| 7 | 7 | 82.5 | $n_D^{20.5}$ 1.5725 | C | 44.26 | 44.54 |
| | | | | H | 5.05 | 5.30 |
| | | | | N | 3.69 | 3.72 |
| | | | | P | 8.15 | 8.45 |
| 8 | 8 | 90.1 | $n_D^{20.5}$ 1.5518 | C | 49.84 | 49.90 |
| | | | | H | 6.70 | 6.65 |
| | | | | N | 3.87 | 3.82 |
| | | | | P | 8.57 | 8.05 |

Example 9: (Compound No. 16)

To a solution of 31.7 g. of potassium 0-(n)-butyl-S-allylphosphorodithioate in 100 ml. of water, were added 18.3 g. of N-methylaniline-α-chloroacetamide, and then the mixture was stirred at 70° C. for 2 hours. Benzene was added to the mixture and the resultant solution. Benzene solution was washed with a 5% sodium carbonate solution and then water. Thereafter benzene was distilled off to obtain 34.2 g. of yellow and oily 0-(n)butyl-S-allyl-S-(N-methyl-N-phenylcarbamoylmethyl)-phosphorodithiolate ($n_D^{20.0}$ 1.5602).

| Elemental analysis: Calculated (%) (as $C_{16}H_{24}NO_3PS_2$) | Found (%) |
|---|---|
| P | 8.29 | 8.65 |
| C | 51.46 | 51.71 |
| H | 6.48 | 6.52 |
| N | 3.75 | 3.86 |

What we claim is:
1. A compound of the formula

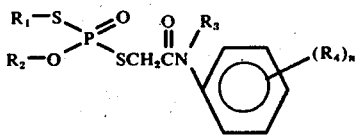

wherein $R_1$ is lower alkenyl, chlorine- or bromine-substituted lower alkenyl, or alkoxyalkyl having 1–2 carbon atoms in the alkoxy group and 1–3 carbon atoms in the alkyl group, $R_2$ is lower alkyl, $R_3$ is lower alkyl, $R_4$ is lower alkyl, lower alkoxy or halogen, and n is zero or an integer of 1 to 5.

2. A compound of the formula

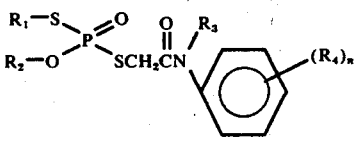

wherein $R_1$ is $C_3 - C_4$ alkenyl, chlorine- or bromine-substituted propenyl or $C_1 - C_2$ alkoxy $C_1 - C_3$ alkyl, $R_2$ is $C_1 - C_4$ alkyl, $R_3$ is $C_1 - C_4$ alkyl, $R_4$ is $C_1 - C_2$ alkyl, methoxy or chlorine, and n is zero or an integer of 1 to 5.

3. A compound of the formula

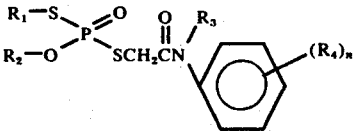

wherein $R_1$ is $C_3 - C_4$ alkenyl, chloroallyl, bromoallyl or $C_1 - C_2$ alkoxy $C_1 - C_2$ allyl, $R_2$ is $C_1 - C_3$ alkyl, $R_3$ is methyl, and n is zero or an integer of 5.

4. A compound of the formula

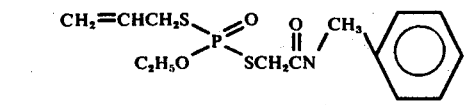

5. A composition comprising an inert carrier and a herbicidally effective amount of at least one phosphorothiolate compound of the formula

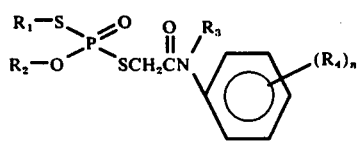

wherein $R_1$ is lower alkenyl, chlorine- or bromine-substituted lower alkenyl, or alkoxyalkyl having 1–2 carbon atoms in the alkoxy group and 1–3 carbon atoms in the alkyl group, $R_{12}$ is lower alkyl, $R_3$ is lower alkyl, $R_4$ is lower alkyl, lower alkoxy or halogen, and n is zero or an integer of 1 to 5.

6. A composition according to claim 5, wherein the composition is in the form of granules, dust, wettable powder or emulsifiable concentrate.

7. A composition according to claim 6, wherein the composition further contains a fertilizer, a fungicide, an insecticide, a nematocide or a herbicide other than a compound of the formula (I), or a mixture thereof.

8. A method of killing weeds which comprises applying to the locus to be treated a herbicidally effective amount of a compound of the formula

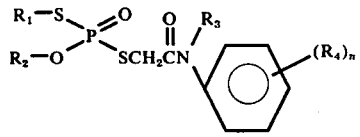

wherein $R_1$ is lower alkenyl, chlorine- or bromine-substituted lower alkenyl, or alkoxyalkyl having 1–2 carbon atoms in alkoxy group and 1–3 carbon atoms in the alkyl group, $R_2$ is lower alkyl, $R_3$ is lower alkyl, $R_4$ is lower alkyl, lower alkoxy or halogen, and n is zero or an integer of 1 to 5.

* * * * *